United States Patent
Sekitani et al.

(10) Patent No.: US 11,707,219 B2
(45) Date of Patent: Jul. 25, 2023

(54) ELECTRODE SHEET AND BIOLOGICAL SIGNAL MEASURING DEVICE INCLUDING ELECTRODE SHEET

(71) Applicant: Osaka University, Suita (JP)

(72) Inventors: Tsuyoshi Sekitani, Suita (JP); Takafumi Uemura, Suita (JP); Teppei Araki, Suita (JP); Shusuke Yoshimoto, Suita (JP)

(73) Assignee: Osaka University, Suita (JP)

( * ) Notice: Subject to any disclaimer, the term of this patent is extended or adjusted under 35 U.S.C. 154(b) by 943 days.

(21) Appl. No.: 16/306,468

(22) PCT Filed: May 25, 2017

(86) PCT No.: PCT/JP2017/019621
§ 371 (c)(1),
(2) Date: Nov. 30, 2018

(87) PCT Pub. No.: WO2017/208977
PCT Pub. Date: Dec. 7, 2017

(65) Prior Publication Data
US 2019/0290158 A1    Sep. 26, 2019

(30) Foreign Application Priority Data

Jun. 3, 2016  (JP) .................................. 2016-112076

(51) Int. Cl.
*A61B 5/05*    (2021.01)
*A61N 1/00*    (2006.01)
(Continued)

(52) U.S. Cl.
CPC ............ *A61B 5/291* (2021.01); *A61B 5/6814* (2013.01); *A61B 5/0006* (2013.01); *A61B 5/374* (2021.01);
(Continued)

(58) Field of Classification Search
CPC .............. A61B 2562/046; A61B 5/259; A61B 2560/0412; A61B 5/0006; A61B 5/25;
(Continued)

(56) References Cited

U.S. PATENT DOCUMENTS 5,755,230 A    5/1998  Schmidt et al.
2005/0096513 A1*  5/2005  Ozguz ................. H01L 21/6836
                                                          438/459
(Continued)

FOREIGN PATENT DOCUMENTS

JP    08-229132 A    9/1996
JP    H11-511367 A   10/1999
(Continued)

OTHER PUBLICATIONS

Mohseni et al. "A Fully Integrated Neural Recording Amplifier With DC Input Stabilization" IEEE Transactions on Biomedical Engineering, vol. 51, No. 5. May 2004 (Year: 2004).*

(Continued)

*Primary Examiner* — Joseph A Stoklosa
*Assistant Examiner* — Brian M Antiskay
(74) *Attorney, Agent, or Firm* — Knobbe, Martens, Olson & Bear, LLP

(57) ABSTRACT

An electrode sheet is capable of suppressing an influence of noise that is applied on a wire, and a biological signal measuring device uses the electrode sheet. The electrode sheet is provided with a sheet, a biological signal receiving electrode formed at the sheet and exposed from the sheet, a biological signal amplifier formed at the sheet, an interface part for connection to an external biological signal processing unit, a first wire that connects the biological signal receiving electrode and an input part of the biological signal (Continued)

amplifier to each other, and a second wire that connects the interface part and an output part of the biological signal amplifier to each other.

9 Claims, 5 Drawing Sheets

(51) Int. Cl.
*A61B 5/291* (2021.01)
*A61B 5/00* (2006.01)
*A61B 5/374* (2021.01)

(52) U.S. Cl.
CPC ......... *A61B 5/72* (2013.01); *A61B 2560/0412* (2013.01); *A61B 2560/0468* (2013.01)

(58) Field of Classification Search
CPC .... A61B 2562/166; A61B 2018/00839; A61B 5/291; A61B 5/24; A61B 5/369; A61B 5/0024; A61B 5/389; A61B 5/30; A61B 5/282; A61B 2562/164; A61B 5/0031; A61B 5/6833; A61B 5/053; A61B 5/0002; A61B 5/6868; A61B 5/6814
USPC ........ 600/372–374, 377–378, 382–384, 386, 600/391, 393, 544–545
See application file for complete search history.

(56) References Cited

U.S. PATENT DOCUMENTS

| | | | |
|---|---|---|---|
| 2009/0129031 A1* | 5/2009 | Someya | G01L 5/00 29/829 |
| 2011/0054583 A1* | 3/2011 | Litt | A61B 5/14552 607/116 |
| 2013/0072775 A1* | 3/2013 | Rogers | A61M 5/31 600/378 |
| 2013/0172722 A1 | 7/2013 | Ninane et al. | |
| 2015/0276430 A1 | 10/2015 | Sekitani et al. | |
| 2016/0007872 A1* | 1/2016 | Bishay | A61B 5/282 600/382 |

FOREIGN PATENT DOCUMENTS

| | | |
|---|---|---|
| JP | 2001-061799 A | 3/2001 |
| WO | WO 2009/114689 A1 | 9/2009 |
| WO | WO 2014/054586 A1 | 4/2014 |

OTHER PUBLICATIONS

Extended European Search Report received in European Patent Application No. 17806534.8 dated Apr. 17, 2019.
Sekitani, T., et al., Ultraflexible Organic Amplifier With Biocompatible Gel Electrodes, Nature Communications 7(1), Apr. 29, 2016, 11 pages.

* cited by examiner

ELECTRODE SHEET AND BIOLOGICAL SIGNAL MEASURING DEVICE INCLUDING ELECTRODE SHEET

TECHNICAL FIELD

The present invention relates to an electrode sheet, and a biological signal measuring device including the electrode sheet.

BACKGROUND ART

A biological signal measuring device conventionally known includes a plurality of electrodes 12, a wire lead 32, and transmitting means 18. The transmitting means 18 includes amplifying means 30, a system controller 44, a transmitter 28, etc. In this biological signal measuring device, brain wave signals (biological signals) received by a plurality of the electrodes 12 are input via the wire lead 32 to the transmitting means 18. The brain wave signals (biological signals) input to the transmitting means 18 are amplified by the amplifying means 30, and then converted to digital signals by an analog-digital converter (A/D converter) in the system controller 44. Then, these signals are transmitted without wires from the transmitter 28 to an operator interface 22. The operator interface 22 analyzes the waveforms of the brain wave signals (biological signals) (see patent document 1).

Patent Document 1: Japanese Unexamined Patent Application (Translation of PCT Application), Publication No. H11-511367

SUMMARY OF THE INVENTION

Problems to be Solved by the Invention

In the biological signal measuring device of patent document 1, the wire lead 32 unintentionally functions as an antenna to receive noise. Hence, the brain wave signals received by a plurality of the electrodes 12 and transmitted via the wire lead 32 are subjected to application of noise received via the wire lead 32. In this way, the brain wave signals received by a plurality of the electrodes 12 are to be influenced by the noise. A brain wave signal has a small amplitude from about 1 to about 10 μV among those of biological signals. This particularly makes the brain wave signal susceptible to the influence of noise.

The number of bits of an A/D converter to be used is required to be increased (to 20 bits or more, for example) for measuring a brain wave signal influenced by noise. However, increasing the number of bits of the A/D converter generally increases the cost of the A/D converter. As described above, a relatively costly measuring device is required for measuring a brain wave signal influenced by noise, which is undesirable. Hence, suppression of influence of noise applied to a wire is desired.

The present invention is intended to provide an electrode sheet capable of suppressing influence of noise applied to a wire. The present invention is further intended to provide a biological signal measuring device using an electrode sheet capable of suppressing influence of noise applied to a wire.

Means for Solving the Problems (1) The present invention relates to an electrode sheet comprising: a sheet; a biological signal receiving electrode formed at the sheet and exposed on the sheet; a biological signal amplifier formed at the sheet; an interface part for connection to an external biological signal processing unit; a first wire formed at the sheet and connecting the biological signal receiving electrode and an input part of the biological signal amplifier; and a second wire formed at the sheet and connecting the interface part and an output part of the biological signal amplifier.

(2) The first wire may have a shorter length than the second wire.

(3) A plurality of the biological signal receiving electrodes and the biological signal amplifiers are formed, and the number of the biological signal receiving electrodes and that of the biological signal amplifiers may be the same.

The sheet may have stretching properties, and the sheet may be less stretchable in an area where the biological signal amplifier is formed than in an area of the sheet where the biological signal amplifier is not formed.

(5) The biological signal amplifier may not be exposed on the sheet.

(6) The first wire may connect the biological signal receiving electrode and the input part of the biological signal amplifier via a DC removing capacitor.

(7) The sheet may have a size falling within the range of a human forehead, and the biological signal amplifier may allow amplification of an AC signal of 10 kHz or less.

(8) The present invention also relates to a biological signal measuring device comprising: the electrode sheet described in any one of (1) to (7); and a biological signal processing unit connected to the interface part. A biological signal received by the biological signal receiving electrode is amplified by the biological signal amplifier, and the amplified biological signal is input to the biological signal processing unit via the interface part. The biological signal processing unit performs predetermined processing on the input biological signal.

Effects of the Invention

According to the present invention, an electrode sheet capable of reducing influence of noise applied to a wire can be provided. According to the present invention, a biological signal measuring device using an electrode sheet capable of reducing influence of noise applied to a wire can be provided.

BRIEF DESCRIPTION OF THE DRAWINGS

FIG. 5A show the circuit configuration of a biological signal amplifier 13 formed to the electrode sheet according to the embodiment of the present invention shows an example of the circuit configuration of the biological signal amplifier, and FIG. 5B shows a different example of the circuit configuration of the biological signal amplifier.

DETAILED DESCRIPTION OF THE
PREFERRED EMBODIMENT

Figure 1:
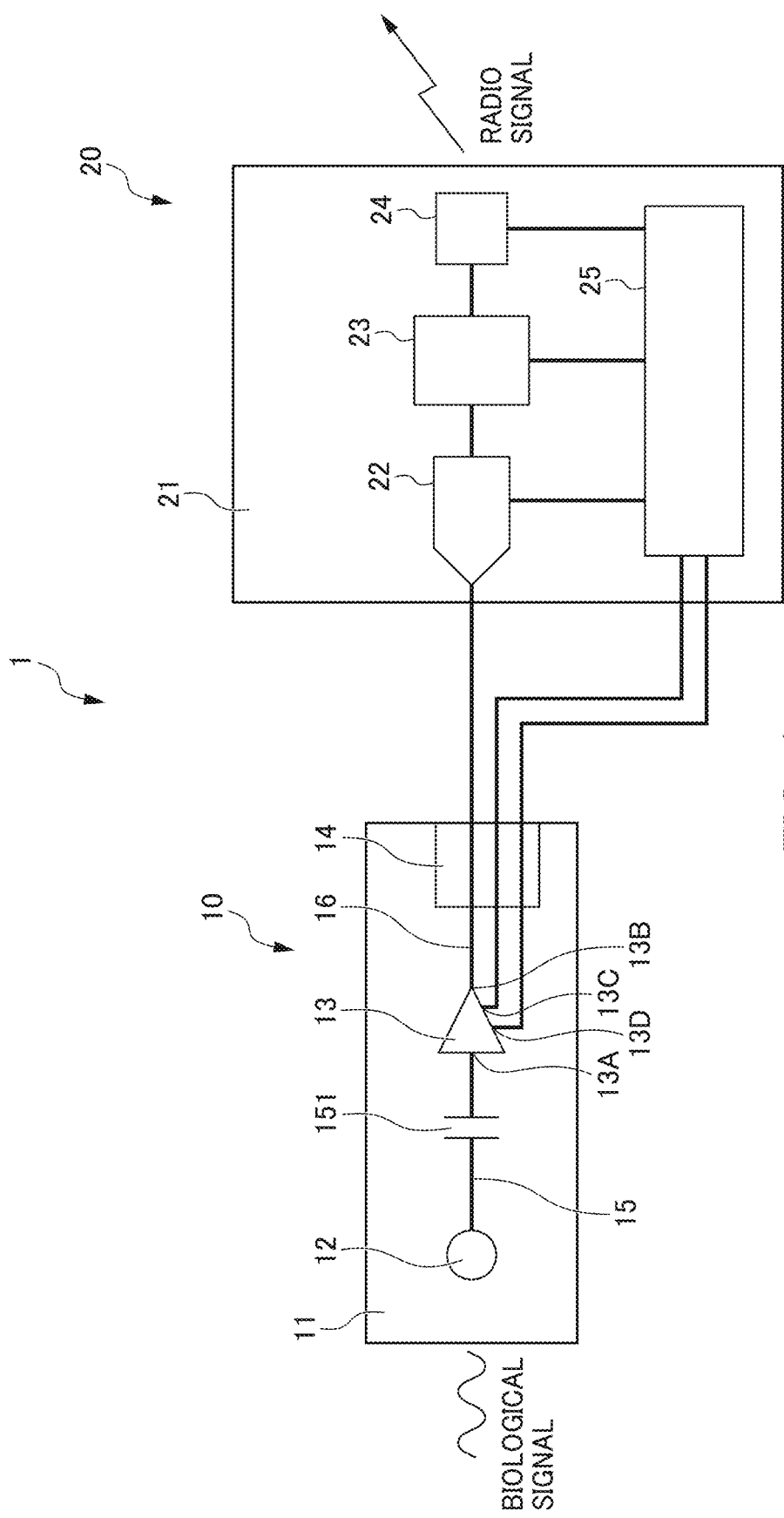
FIG. 1 is a block diagram of a biological signal measuring device according to an embodiment of the present invention.
Figure 2:
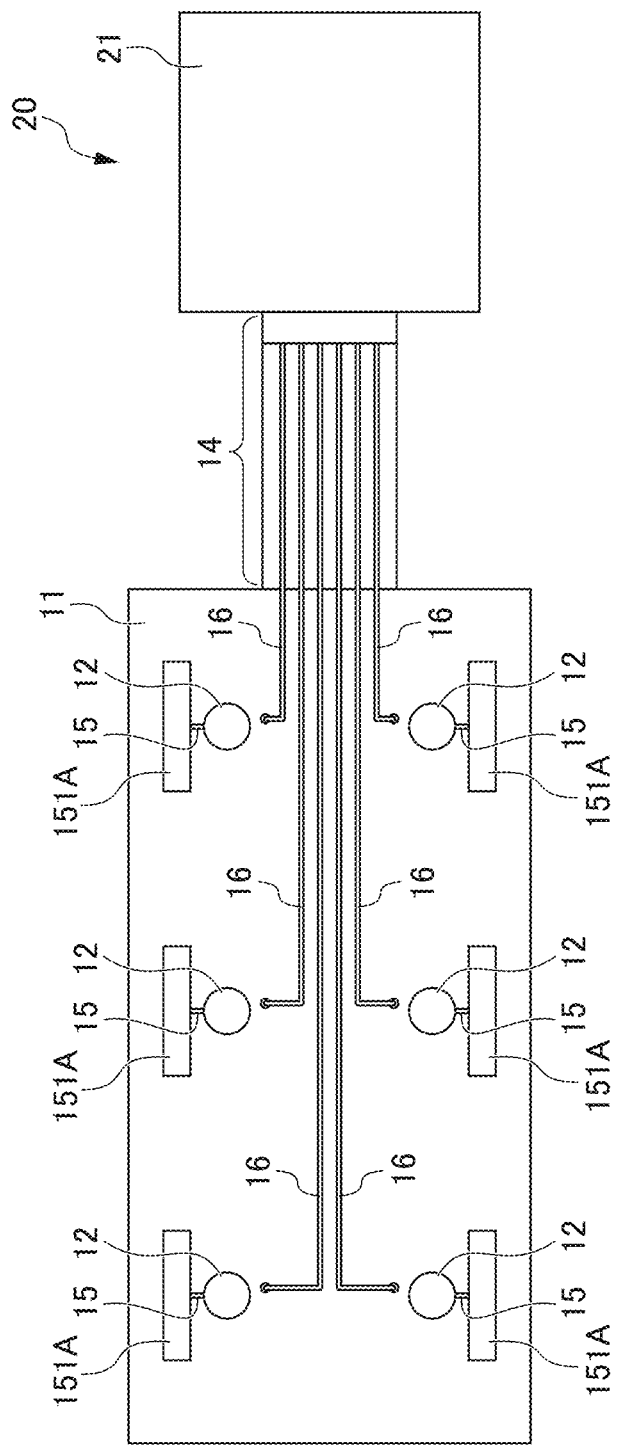
FIG. 2 is an external view of the biological signal measuring device according to the embodiment of the present invention.
Figure 3:
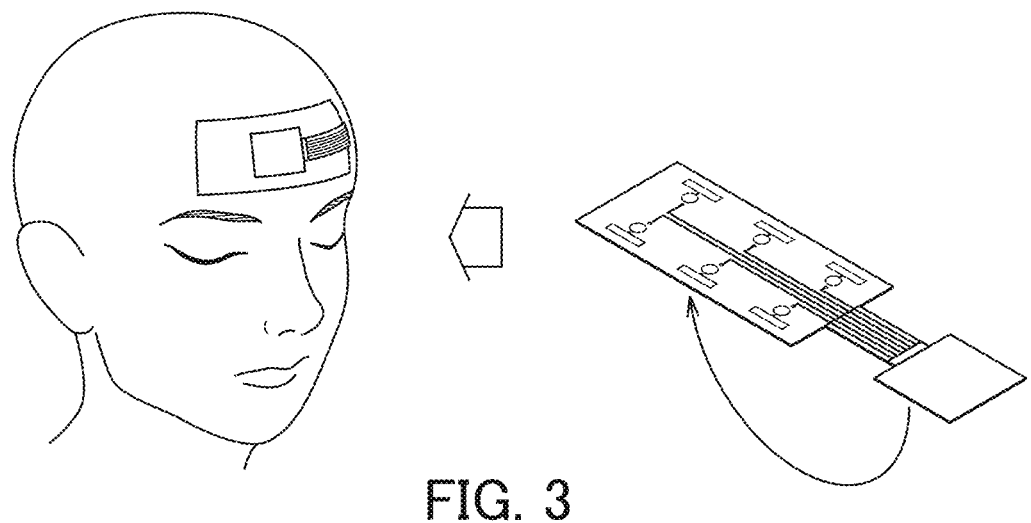
FIG. 3 shows an example of attachment of the biological signal measuring device according to the embodiment of the present invention to a test subject.

An embodiment of the present invention will be described below by referring to the drawings. FIG. 1 is a block diagram of a biological signal measuring device according to the embodiment of the present invention. FIG. 2 is an external view of the biological signal measuring device according to the embodiment of the present invention. FIG. 3 shows an example of attachment of the biological signal measuring device according to the embodiment of the present invention to a test subject.

As shown in FIGS. 1 and 2, a biological signal measuring device 1 includes an electrode sheet 10 and a biological signal processing unit 20. The electrode sheet 10 includes a stretchable sheet 11 as a sheet, a biological signal receiving electrode 12, a biological signal amplifier 13, an interface part 14, a first wire 15, a DC removing capacitor 151, a second wire 16, a power supply line 17, and a ground supply line 18. As shown in FIG. 1, the biological signal processing unit 20 includes a mounting board 21, an A/D converter 22, a digital signal processor 23, a radio part 24, and a power supply management part 25. A filter (band-pass filter, high-pass filter, low-pass filter, for example) (not shown) is provided appropriately in a former stage of the A/D converter.

In FIG. 1, for simplification of the illustration, the biological signal receiving electrode 12, the biological signal amplifier 13, the first wire 15, the DC removing capacitor 151, the second wire 16, the power supply line 17, and the ground supply line 18 which belong to only one system are shown. As shown in FIG. 2, however, six systems (a plurality of systems) are prepared in this embodiment each including the biological signal receiving electrode 12, the biological signal amplifier 13, the first wire 15, the DC removing capacitor 151, the second wire 16, the power supply line 17, and the ground supply line 18.

The illustrations of the A/D converter 22, the digital signal processor 23, the radio part 24, and the power supply management part 25 are omitted from FIG. 2. The positions of the A/D converter 22, the digital signal processor 23, the radio part 24, and the power supply management part 25 mounted on the mounting board 21 can be changed in various ways. In FIG. 2, the illustrations of the power supply line 17 and the ground supply line 18 are omitted for the sake of simplification.

FIG. 2 shows a DC removing capacitor input side electrode 151A as one electrode of the DC removing capacitor 151. The DC removing capacitor input side electrode 151A is arranged near the biological signal receiving electrode 12 and has a rectangular shape. The entire configuration of the DC removing capacitor 151 will be described later by referring to FIG. 4. The biological signal amplifier 13 is provided inside the stretchable sheet 11, so that it is not shown in FIG. 2. The arrangement of the biological signal amplifier 13 will be described later by referring to FIG. 4.

The stretchable sheet 11 is a sheet capable of stretching in all directions, and can be made of various types of materials having stretching properties. In this embodiment, the stretchable sheet 11 has a size falling within the range of a human forehead. The size falling within the range of a human forehead means a size failing within the range of a rectangle of 5 cm×15 cm, for example. The stretchable sheet 11 has adhesion properties.

If the shape of the biological signal amplifier 13 or that of the DC removing capacitor 151 changes in response to stretching, the signal amplifying characteristics (including a gain at each frequency, for example) of the biological signal amplifier 13 may change. Breakage of the biological signal amplifier 13 may also occur. In this regard, the stretchable sheet 11 is less stretchable in an area where the biological signal amplifier 13 is formed and in an area where the DC removing capacitor 151 is formed than in the other area of the stretchable sheet 11 (including an area where the biological signal amplifier 13 is formed and an area where the DC removing capacitor 151 is not formed). Specifically, the stretchable sheet 11 as a whole has stretching properties, and has two areas having different stretching properties. These different areas can be made of materials using different stretching properties.

The biological signal receiving electrode 12 is a circular stretchable conductor printed on the stretchable sheet 11. The stretchable conductor is a conductor formed by using a silver nanowire, for example. The biological signal receiving electrode 12 is capable of stretching to follow stretching of the stretchable sheet 11. As shown in FIG. 2, six (a plurality of) biological signal receiving electrodes 12 are formed on the stretchable sheet 11. The biological signal receiving electrodes 12 are exposed on the stretchable sheet 11.

The biological signal amplifier 13 includes an input part 13A, an output part 13B, a power supply terminal 13C, and a ground terminal 13D. The biological signal amplifier 13 is operated by supply of a predetermined voltage to the power supply terminal 13C and supply of a ground potential to the ground terminal 13D. The biological signal amplifier 13 amplifies a biological signal input to the input part 13A, and outputs the amplified biological signal from the output part 13B. The biological signal amplifier 13 is an amplifier capable of amplifying an AC signal of 10 kHz or less linearly. The biological signal amplifier 13 does not amplify an AC signal higher than 10 kHz (does not have a positive gain). The biological signal amplifier 13 is provided inside the stretchable sheet 11 (as will be described later by referring to FIG. 4). Allowing linear amplification means allowing amplification of an input signal so as to retain the input signal to such a degree that the amplitude or phase of the input signal can be analyzed by the biological signal processing unit 20. Further, 10 kHz is a frequency component that can be detected from the forehead of a test subject who has developed an epileptic symptom. Allowing analysis of a frequency of 10 kHz or less means allowing analysis of frequency components in nearly all brain wave signals. If an epileptic symptom is not required to be detected, the biological signal amplifier 13 may be an amplifier capable of amplifying an AC signal or 1 kHz or less linearly.

The interface part 14 is a unit provided at the electrode sheet 10 for connecting the electrode sheet 10 to the external biological signal processing unit 20. The interface part 14 includes a bridge section 14A and a connector 14B. The bridge section 14A is connected to the stretchable sheet 11. The bridge section 14A is also made of a material having stretching properties. The bridge section 14A may be formed integrally with the stretchable sheet 11. A connector used in general portable electronic devices can be used as the connector 14B.

The first wire 15 is a wire connecting the biological signal receiving electrode 12 and the input part 13A of the biological signal amplifier 13. In this embodiment, the first wire 15 connects the biological signal receiving electrode 12 and the input, part 13A of the biological signal amplifier 13 via the DC removing capacitor 151. In this embodiment, the first wire 15 includes a wire closer to the biological signal receiving electrode 12 side than the DC removing capacitor 151 (a wire connecting the biological signal receiving electrode 12 and the DC removing capacitor input side electrode 151A), and a wire closer to the biological signal amplifier 13 than the DC removing capacitor 151 (a wire connecting a DC removing capacitor output side electrode 151B and the biological signal amplifier 13).

The DC removing capacitor 151 is connected in series with the biological signal receiving electrode 12 and the input part of the biological signal amplifier 13 and between the biological signal receiving electrode 12 and the input part of the biological signal amplifier 13. The DC removing capacitor 151 is a capacitor for removing a DC component from a biological signal. In this embodiment, the first wire 15 connects the biological signal receiving electrode 12 and the input part 13A of the biological signal amplifier 13 in an alternating manner.

The second wire 16 is a wire connecting the output part 13B of the biological signal amplifier 13 and the interface part 14. The first wire 15 is shorter than the second wire 16.

The power supply line 17 is a wire connecting the power supply terminal 13C of the biological signal amplifier 13 and the interface part 14. The ground supply line 18 is a wire connecting the ground terminal 13D of the biological signal amplifier 13 and the interface part 14.

Like the biological signal receiving electrode 12, the first wire 15, the DC removing capacitor 151, the second wire 16, the power supply line 17, and the ground supply line 18 are stretchable conductors such as silver nanowires printed on the stretchable sheet 11. Like the biological signal receiving electrode 12, the first wire 15, the second wire 16, the power supply line 17, and the ground supply line 18 are capable of stretching to follow stretching of the stretchable sheet 11. As described above, however, the DC removing capacitor 151 is formed in a less stretchable area of the stretchable sheet 11. Thus, while the DC removing capacitor 151 is made of a stretchable material, the DC removing capacitor 151 does not stretch in the same manner as the first wire 15, the second wire 16, the power supply line 17, and the ground supply line 18.

Boards such as a general printed wiring board without flexibility, a flexible hoard having flexibility, etc. are available as the mounting board 21. The A/D converter 22 has the function of converting an analog signal to a digital signal. A relatively inexpensive A/D converter of the number of bits such as eight is used as the A/D converter 22. The digital signal processor 23 is a circuit that performs predetermined processing on the digital signal. The radio part 24 is a circuit for radio communication with an external computer (server or smartphone, for example). A Bluetooth (registered trademark) module or a Wi-Fi module is used as the radio part 24, for example.

The power supply management part 25 is a circuit that supplies a power supply potential and a ground potential to the A/D converter 22, the digital signal processor 23, and the radio part 24. The power supply management part 25 supplies the power supply potential and the ground potential further to the biological signal amplifier 13 via the interface part 14. The power supply line 17 is used for supply of the power supply potential. The ground supply line 18 is used for supply of the ground potential.

A way of using the biological signal measuring device 1 will be described next by referring to FIG. 3. The biological signal measuring device 1 is folded at the bridge section 14A of the interface part 14. In this way, the biological signal processing unit 20 is stacked on the stretchable sheet 11. The biological signal processing unit 20 stacked on the electrode sheet 10 is fixed to the stretchable sheet 11 with an adhesive gel material (not shown), for example.

The biological signal measuring device 1 folded in this way is attached to the forehead of a test subject in such a manner that the exposed biological signal receiving electrode 12 comes into tight contact with the forehead. With the adhesion properties of the stretchable sheet 11, the biological signal measuring device 1 is fixed to the forehead of the test subject. While the biological signal measuring device 1 is fixed to the forehead of the test subject, the biological signal measuring device 1 acquires a human brain wave from the biological signal receiving electrode 12.

The motion of the biological signal measuring device 1 will be described next by referring to FIG. 1. A brain wave received by the biological signal receiving electrode 12 is input to the biological signal amplifier 13 via the first wire 15 and the DC removing capacitor 151. The biological signal amplifier 13 amplifies the input biological signal linearly. The amplified biological signal is output to the biological signal processing unit 20 via the second wire 16 and the interface part 14.

The biological signal is converted by the A/D converter 22 in the biological signal processing unit 20 to a digital signal, and output to the digital signal processor 23. The digital signal processor 23 performs predetermined processing on the digital signal. After implementation of the predetermined processing, the digital signal is output to the radio part 24. The radio part 24 transmits the digital signal as a radio signal to the external computer.

The radio part 24 is capable of receiving an instruction signal without wires coming from the external computer. The instruction signal is a signal for instructing various motions of the biological signal processing unit 20, for example. The radio part 24 outputs the instruction signal to the digital signal processor 23, etc. The digital signal processor 23 is capable of changing the content or timing of signal processing based on the instruction signal.

In the biological signal measuring device 1, the biological signal amplifier 13 is arranged at the electrode sheet 10 side. Thus, a brain wave signal of a small amplitude (on the order of microvolts, for example) received by the biological signal receiving electrode 12 is amplified immediately to a signal of a large amplitude (on the order of millivolts). Thus, even if the second wire 16 functions as an antenna to receive noise and noise is applied to a brain wave signal transmitted via the second wire 16, the brain wave signal has already been given a large amplitude. As a result, influence by the noise is not serious.

In the biological signal measuring device 1, noise applied to the first wire 15 can also exert relatively serious influence on a brain wave signal. In the biological signal measuring device 1, however, the shorter length of the first wire 15 than the second wire 16 reduces influence of noise applied to a biological signal before being amplified. In this way, by the use of the electrode sheet 10 equipped with the biological signal amplifier 13, it becomes possible to suppress influence of noise.

In the case of the biological signal measuring device in patent document 1, a brain wave signal is amplified after every noise received via the wire lead 32 is applied to the brain wave signal. This makes the brain wave signal being buried in the noise. Converting the brain wave signal buried in the noise to a digital signal necessarily requires an A/D converter of a relatively wide dynamic range (20 bits or more, for example).

By contrast, in the biological signal measuring device 1 of this embodiment, the biological signal amplifier 13 suppresses influence of noise. Thus, a biological signal becomes unlikely to be buried in the noise. As a result, an A/D converter of a relatively narrow dynamic range (about eight bits, for example) becomes available. In this way, a relatively inexpensive A/D converter becomes available as the A/D converter 22 in the biological signal processing unit 20.

Figure 4:
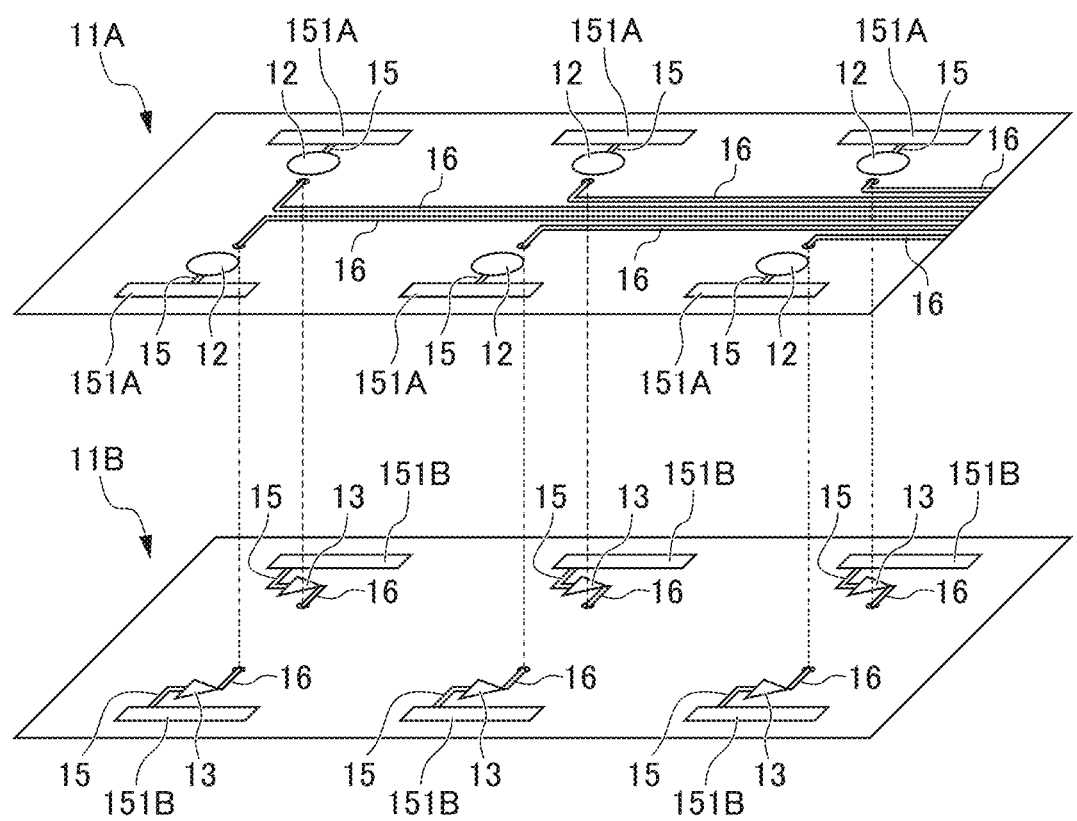
FIG. 4 is an exploded perspective view of an electrode sheet according to the embodiment of the present invention.

The configuration of the electrode sheet 10 will be described next by referring to FIG. 4. FIG. 4 is an exploded perspective view of the electrode sheet according to the embodiment of the present invention. The stretchable sheet 11 forming the electrode sheet 10 includes a first stretchable sheet 11A and a second stretchable sheet 11B. The stretchable sheet 11 shown in FIG. 2 is a part belonging to the first stretchable sheet 11A side of the stretchable sheet 11.

The biological signal receiving electrode 12, the first wire 15, the DC removing capacitor input side electrode 151A, and the second wire 16 are formed by printing on the first stretchable sheet 11A. As described above, the stretchable sheet 11A is less stretchable in an area where the DC removing capacitor input side electrode 151A is formed than in the other area of the stretchable sheet 11A.

The DC removing capacitor output side electrode 151B (the other electrode of the DC removing capacitor 151) and the biological signal amplifier 13 are arranged at the second stretchable sheet 11B. Six (a plurality of) biological signal amplifies 13 are formed. The number of the biological signal amplifiers 13 is the same as that of the biological signal receiving electrodes 12. For the sake of simplification, the biological signal amplifiers 13 are shown as symbols. An example of the circuit configuration of the biological signal amplifiers 13 will be described later by referring to FIG. 5A and FIG. 5B.

As described above, the second stretchable sheet 11B is less stretchable in an area where the biological signal amplifier 13 is formed and in an area where the DC removing capacitor output side electrode 151B is formed than in the other area of the stretchable sheet 11B. For example, in the second stretchable sheet 11B, the area with the biological signal amplifier 13 is formed so as to be capable of stretching only to a degree that makes change in characteristics of the biological signal amplifier 13 ignorable.

The first stretchable sheet 11A has stretching properties except the area where the DC removing capacitor input side electrode 151A is formed. In the second stretchable sheet 11B, an area without the biological signal amplifier 13 or an area without the DC removing capacitor output side electrode 151B has stretching properties substantially the same (or exactly the same) as those of the first stretchable sheet 11A. The shape of the first stretchable sheet 11A and that of the second stretchable sheet 11B are substantially the same (or exactly the same). The first stretchable sheet 11A and the second stretchable sheet 11B are stacked and tightly fixed to each other. As a result, the first stretchable sheet 11A and the second stretchable sheet 11B become available as one electrode sheet 10. The biological signal amplifier 13 is formed at the second stretchable sheet 11B and is covered by the first stretchable sheet 11A. Thus, the biological signal amplifier 13 is not exposed on the stretchable sheet 11.

The first stretchable sheet 11A and the second stretchable sheet 11B are stacked on each other to make the DC removing capacitor input side electrode 151A and the DC removing capacitor output side electrode 151B face each other. The DC removing capacitor output side electrode 151B has the same size as the DC removing capacitor input side electrode 151A and has the same rectangular shape as the DC removing capacitor input side electrode 151A. The DC removing capacitor input side electrode 151A and the DC removing capacitor output side electrode 151B facing each other together function as one DC removing capacitor 151. The output part 13B of the biological signal amplifier 13 and the second wire 16 of the first stretchable sheet 11A are connected via a penetration electrode formed at the first stretchable sheet 11A. The penetration electrode is indicated by a dotted line in FIG. 4.

As described above, the area of the first stretchable sheet 11A where the DC removing capacitor input side electrode 151A is formed, the area of the second stretchable sheet 11B where the DC removing capacitor output side electrode 151B is formed, and the area of the second stretchable sheet 11B where the biological signal amplifier 13 is formed, are less stretchable than the other areas. Thus, as viewed from the stretchable sheet 11 as a whole formed by stacking the first stretchable sheet 11A and the second stretchable sheet 11B, the area where the DC removing capacitor 151 is formed and the area where the biological signal amplifier 13 is formed are less stretchable than the other area.

The illustrations of the power supply line 17 and the ground supply line 18 are also omitted from FIG. 4. The power supply line 17 and the ground supply line 18 may be formed at the first stretchable sheet 11A, at the second stretchable sheet 11B, or at the first stretchable sheet 11A and the second stretchable sheet 11B.

Figure 5A:
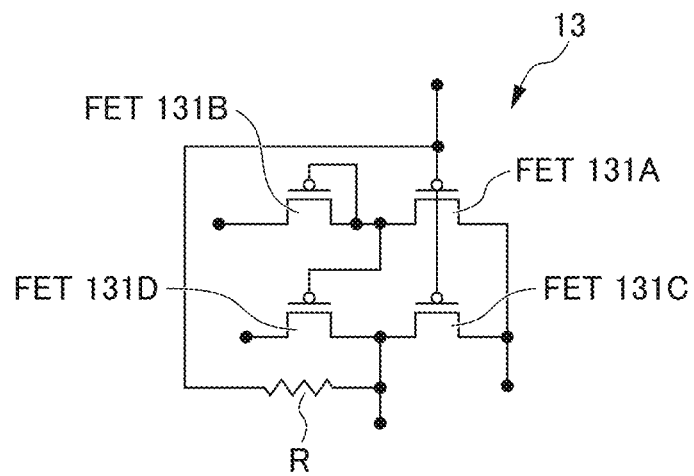
FIG. 5A and FIG. 5B show the circuit configuration of a biological signal amplifier 13 formed to the electrode sheet according to the embodiment of the present invention.
Figure 5B:
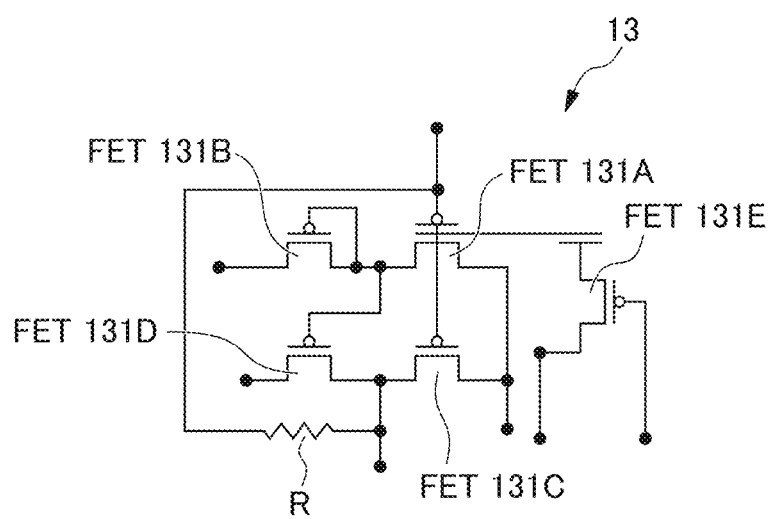

The circuit configuration of the biological signal amplifier 13 will be described next by referring to FIG. 5A and FIG. 5B. FIG. 5A shows an example of the circuit configuration of the biological signal amplifier 13 formed at the electrode sheet according to the embodiment of the present invention. FIG. 5B shows a different example of the circuit configuration of the biological signal amplifier 13 formed at the electrode sheet according to the embodiment of the present invention.

As shown in FIG. 5A, the biological signal amplifier 13 includes four FETs 131A to 131D, and a resistor R. Each of the four FETs 131A to 131D is a P-type electric field effect transistor. The input part of the biological signal amplifier 13 corresponds to the gate of the FET 131A and the gate of the FET 131C. The output part of the biological signal amplifier 13 corresponds to a connection between the FET 131C and the FET 131D. The resistor R has one end connected to the gate of the FET 131A and the gate of the FET 131C, and an opposite end connected to the connection between the FET 131C and the FET 131D. The resistor R is a feedback resistor. The four FETs 131A to 131D form an inverter, and the input and the output of the inverter are connected via the feedback resistor R, thereby forming the biological signal amplifier 13 functioning as a whole as a linear amplifier.

As shown in FIG. 5B, an adjustment FET 131E may be added further to configure the biological signal amplifier 13 as an amplifier with an adjustment function. Adding the adjustment FET 131E allows stabilization of the characteristics of the biological signal amplifier 13. An adjustment signal for the adjustment FET 131E can be supplied from the biological signal processing unit 20 via the interface part 14.

Figure 6:
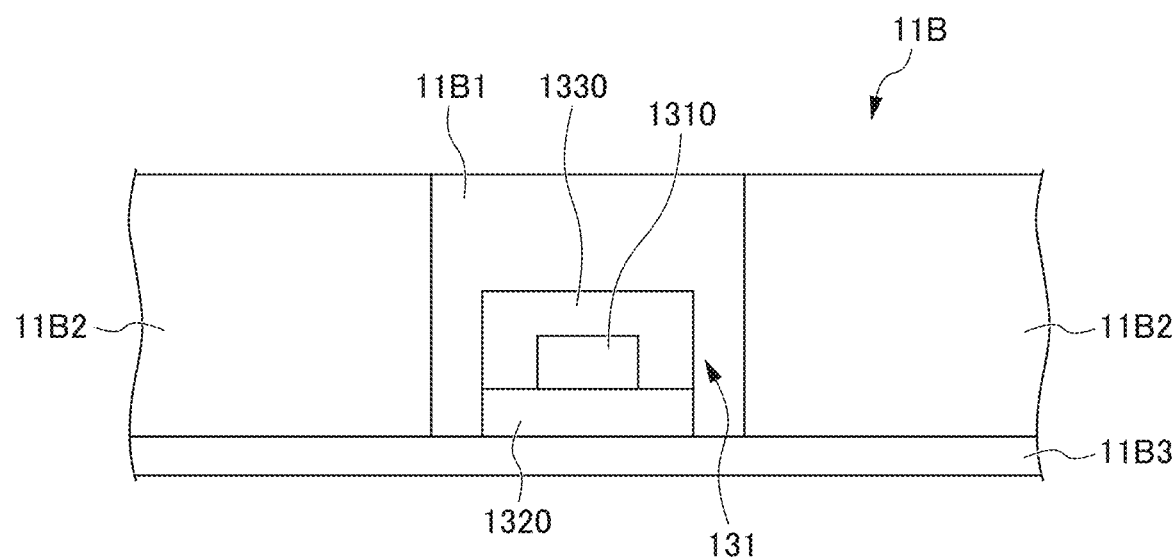
FIG. 6 is a sectional view showing an area where an FET forming the biological signal amplifier 13 is formed at a second stretchable sheet of the electrode sheet according to the embodiment of the present invention.

FIG. 6 is a sectional view showing an area where an FET as a part of the biological signal amplifier 13 is formed at the second stretchable sheet 11B. The second stretchable sheet 11B includes an FET sealing part 11B1, an FET non-sealing part 11B2, and a base part 11B3.

The FET 131 is provided in (arranged at) the FEE sealing part 11B1. The FET non-sealing part 11B2 is a part in which the FET 131 is not provided (at which the FET 131 is not arranged). The base part 11B3 is a film-like member common to the FET sealing part 11B1 and the FET non-sealing part 11B2 and provided under the FET sealing part 11B1 and the FET non-sealing part 11B2.

The FET non-sealing part 11B2 and the base part 11B3 are members having substantially the same (or exactly the same) stretching properties. The FET sealing part 11B1 is a member having the properties of stretching only to a degree that makes change in characteristics of the FET 131 ignorable. The FET sealing part 11B1 is a part included in the foregoing area of the second stretchable sheet 11B where the biological signal amplifier 13 is formed.

The FET 131 includes an FET body part 1310, an FET substrate part 1320, and an FET sealing part 1330. The FET body part 1310 is a semiconductor element part to function as an FET. The configuration of the FET body part 1310 will be described later by referring to FIG. 7. The FET substrate part 1320 is a substrate for arrangement of the FET body part 1310. The FET sealing part 1330 is a part for sealing the FET body part 1310.

As a result of the foregoing configuration of the second stretchable sheet 11B, the second stretchable sheet 11B as a whole has stretching properties. Meanwhile, the second stretchable sheet 11B is less stretchable at the FET sealing part 11B1 (an area with the biological signal amplifier 13) than at the FET non-sealing part 11B2 (an area without the biological signal amplifier 13).

Figure 7:
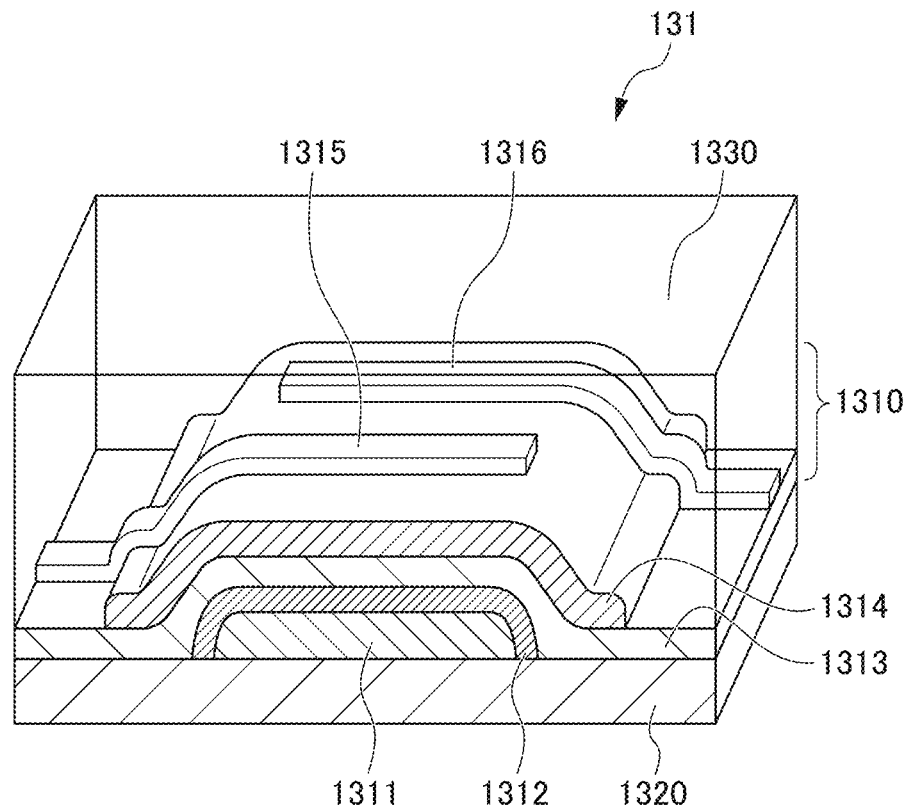
FIG. 7 is a perspective view of the FET forming the biological signal amplifier at the electrode sheet according to the embodiment of the present invention.

The configuration of the FET 131 will be described next by referring to FIG. 7. FIG. 7 shows the configuration of the FET 131. As described above, the FET 131 includes the FET body part 1310, the FET substrate part 1320, and the FET sealing part 1330.

The FET body part 1310 includes a gate electrode 1311, an oxide film 1312, a modifying film 1313, an organic semiconductor layer 1314, a source electrode 1315, and a drain electrode 1316. As shown in FIG. 7, the FET body part 1310 has the configuration of a thin film transistor formed by stacking the gate electrode 1311, the oxide film 1312, the modifying film 1313, and the organic semiconductor layer 1314 in this order, and finally stacking the source electrode 1315 and the drain electrode 1316.

As an example, the gate electrode 1311 can be made of aluminum. As an example, the oxide film 1312 can be made of an aluminum oxide film. As an example, the modifying film 1313 can be formed using a self-assembled monolayer (SAM). The self-assembled monolayer means organic molecules to form a monomolecular film in a self-assembled manner in response to dip of a substrate into a solution, for example. The self-assembled monolayer is a film generally used for surface modification, etc. More specifically, n-octadecylphosphonic acid (C-18) is available. As an example, dinaphthothienothiophene (DNTT) is available as the organic semiconductor layer 1314. As an example, gold electrodes are available as the source electrode 1315 and the drain electrode 1316. Modifying the aluminum oxide film 9 with the modifying layer made of the self-assembled monolayer forms a hybrid gate insulating film. As a result, the FET body part 1310 becomes an organic FET capable of being driven at 3 V.

The foregoing organic FET suppresses electron mobility reduction due to strain, compared to silicon-based semiconductor, for example. Thus, this organic FET is used preferably as an FET provided inside the stretchable sheet.

The electrode sheet 10 of this embodiment includes: the stretchable sheet 11; the biological signal receiving electrode 12 formed at the stretchable sheet 11 and exposed on the stretchable sheet 11; the biological signal amplifier 13 formed at the stretchable sheet 11; the interface part 14 for connection to the external biological signal processing unit 20; the first wire 15 formed at the stretchable sheet 11 and connecting the biological signal receiving electrode 12 and the input part 13A of a plurality of the biological signal amplifiers 13; and the multiple second wires 16 formed at the stretchable sheet 11 and connecting the interface part 14 and the output part 13B of the biological signal amplifier 13. Thus, the electrode sheet 10 of this embodiment is capable of suppressing influence of noise applied to a wire.

In the electrode sheet 10 of this embodiment, the first wire 15 has a shorter length than the second wire 16. Thus, the electrode sheet 10 of this embodiment is capable of more efficiently suppressing influence of noise applied to a wire.

In the electrode sheet 10 of this embodiment, the biological signal receiving electrode 12 and the biological signal amplifier 13 include six (multiple) biological signal receiving electrodes 12 and six (a plurality of) biological signal amplifiers 13. The number of the biological signal receiving electrodes 12 and that of the biological signal amplifiers 13 are both six. Thus, the electrode sheet 10 of his embodiment is capable of measuring brain waves from biological signals in variety of ways. Further, the electrode sheet 10 of this embodiment becomes capable of measuring brain waves highly accurately from biological signals.

In the electrode sheet 10 of this embodiment, the stretchable sheet 11 is less stretchable in an area where the biological signal amplifier 13 is formed than in an area of the stretchable sheet 11 where the biological signal amplifier 13 is not formed. Further, in the electrode sheet 10 of this embodiment, the biological signal amplifier 13 is not exposed on the stretchable sheet 11. As a result, the electrode sheet 10 of this embodiment can become easier to handle.

In the electrode sheet 10 of this embodiment, the first wire 15 connects the biological signal receiving electrode 12 and the input part 13A of the biological signal amplifier 13 via the DC removing capacitor 151. Thus, the electrode sheet 10 of this embodiment makes it possible to amplify a biological signal more accurately.

In the electrode sheet 10 of this embodiment, the stretchable sheet 11 has a size falling within the range of a human forehead, and the biological signal amplifier 13 allows amplification of an AC signal of 10 kHz or less. Thus, the electrode sheet 10 of this embodiment can provide an electrode sheet optimum for measurement of a brain wave signal.

The biological signal measuring device 1 of this embodiment includes the electrode sheet 10, and the biological signal processing unit 20 connected to the interface part 14. A biological signal received by the biological signal receiving electrode 12 is amplified by the biological signal amplifier 13, and the amplified biological signal is input to the biological signal processing unit 20 via the interface part 14. The biological signal processing unit 20 performs predetermined processing on the input biological signal. Thus, the biological signal measuring device 1 is capable of suppressing influence of noise applied to a wire.

The embodiment of the present invention has been described above. However, the present invention should not be limited to the foregoing embodiment but can be changed in various ways within the technical scope described in the claims.

In the foregoing embodiment, the stretchable sheet 11 is used. However, a sheet without stretching properties is available instead of the stretchable sheet 11. Further, the stretchable sheet 11 may be a sheet without adhesion properties. If the stretchable sheet 11 does not have adhesion properties, the stretchable sheet 11 can be fixed to a human forehead with a headband, for example. Further, a sheet without stretching properties and adhesion properties is available instead of the stretchable sheet 11. For example, a flexible sheet (a sheet having flexibility) lacking in one or both of stretching properties and adhesion properties is available instead of the stretchable sheet 11.

In the foregoing embodiment, the first wire 15 has a shorter length than the second wire 16. However, this is not the only case. Even if the length of the first wire 15 is equal to or greater than the length of the second wire 16, influence of noise can still be suppressed. The reason for this is that, even if the length of the first wire 15 is equal to or greater than the length of the second wire 16, the presence of the biological signal amplifier 13 allows suppression of influence of noise, compared to a case in the absence of the biological signal amplifier 13.

In the foregoing embodiment, the biological signal amplifier allows amplification of an AC signal of 10 kHz or less. However, this is not the only case. The biological signal amplifier 13 may allow amplification of an AC signal of 1 kHz or less. The reason for this is as follows. Except for a test subject who is to develop an epileptic symptom, a frequency component in a brain wave measurable from a test subject does not exceed 1 kHz. Thus, allowing amplification of an AC signal of 1 kHz or less means allowing amplification of frequency components in nearly all brain wave signals.

In the foregoing embodiment, six systems (a plurality of systems) are prepared each including the biological signal receiving electrode 12, the biological signal amplifier 13, the first wire 15, the DC removing capacitor 151, the second wire 16, the power supply line 17, and the ground supply line 18. Alternatively, only one system may be prepared, if necessary. The biological signal receiving electrode 12, the first wire 15, the second wire 16, the DC removing capacitor 151, etc. are not limited to their shapes and arrangements described in the foregoing embodiment. Regarding the DC removing capacitor input side electrode 151A and the DC removing capacitor output side electrode 151B, for example, the shapes thereof are rectangles. However, various shapes (square, circle, oval, etc.) are applicable in response to a requested capacity of the DC removing capacitor 151. The DC removing capacitor input side electrode 151A may have a square-cornered U-shape surrounding the biological signal receiving electrode 12, and the DC removing capacitor output side electrode 151B facing the DC removing capacitor input side electrode 151A may have the same square-cornered U-shape. Further, the arrangement and circuit configuration of the biological signal amplifier 13, and the configuration, material, etc. of the FET, are not limited to those described in the foregoing embodiment.

The number of the biological signal receiving electrodes 12 and that of the biological signal amplifiers 13 are both six (same number). However, this is not the only case. An some cases, the number of the biological signal amplifiers 13 can be smaller than that of the biological signal receiving electrodes 12. If a particular biological signal receiving electrode 12 is intended to receive a biological signal of a large amplitude, for example, the biological signal amplifier 13 is not always required to be connected to the particular biological signal receiving electrode 12.

In the foregoing embodiment, the DC removing capacitor 151 is used. In some cases, however, the DC removing capacitor 151 may be omitted in a manner that depends on a biological signal to be measured or the configuration of the biological signal amplifier 13.

In the foregoing embodiment, a biological signal to be measured is a brain wave signal. However, this is not the only case. A biological signal to be measured may be a biological signal other than a brain wave signal such as a signal indicating fluctuations in myoelectric potential (myoelectric potential signal), for example.

EXPLANATION OF REFERENCE NUMERALS

1 Biological signal measuring device
10 Electrode sheet
11 Stretchable sheet (sheet)
12 Biological signal receiving electrode
13 Biological signal amplifier
13A Input part
13B Output part
14 Interface part
15 First wire
151 DC removing capacitor
16 Second wire
20 Biological signal processing unit

What is claimed is:

1. An electrode sheet comprising:
    a first sheet comprising a material, the material having two areas having different stretching properties;
    a second sheet on which a biological signal processor is formed;
    a biological signal receiving electrode formed at the first sheet and exposed on the first sheet;
    a biological signal amplifier formed at the less area of the first sheet;
    an interface part for connection to the biological signal processor;
    a first wire formed at the first sheet and connecting the biological signal receiving electrode and an input part of the biological signal amplifier; and
    a second wire formed at the first sheet and connecting the interface part and an output part of the biological signal amplifier,
    wherein the first sheet comprises:
    a first stretchable sheet on which the biological signal receiving electrodes, the first wire, and the second wire are formed; and
    a second stretchable sheet on which the biological signal amplifiers are arranged.

2. The electrode sheet according to claim 1, wherein the first wire has a shorter length than the second wire.

3. The electrode sheet according to claim 1, wherein
    a number of a plurality of the biological signal receiving electrodes and that of a plurality of the biological signal amplifiers are the same.

4. The electrode sheet according to claim 1, wherein the biological signal amplifier is not exposed on the stretchable sheet.

5. The electrode sheet according to claim 1, wherein the first wire connects the biological signal receiving electrode and the input part of the biological signal amplifier via a direct current (DC) removing capacitor.

6. The electrode sheet according to claim 1, wherein the stretchable sheet has a size of an area falling within a range of a human forehead, and the biological signal amplifier allows amplification of an alternating current (AC) signal of 10 kHz or less.

7. The electrode sheet according to claim 1, wherein
a biological signal received by the biological signal receiving electrode is amplified by the biological signal amplifier, the amplified biological signal is input to the biological signal processor via the interface part, and
the biological signal processor performs predetermined processing on the input biological signal.

8. The electrode sheet according to claim 1, wherein the first stretchable sheet is stacked on the second stretchable sheet.

9. The electrode sheet according to claim 1, wherein the second sheet is stacked on a first surface of the second stretchable sheet opposite to a second surface of the second stretchable sheet on which the biological signal amplifiers are formed such that the biological signal processor is sandwiched and covered by the first surface of the second stretchable sheet and the second sheet.

* * * * *